(12) United States Patent
Maeda et al.

(10) Patent No.: US 8,710,491 B2
(45) Date of Patent: Apr. 29, 2014

(54) FORMING AGENT FOR GATE INSULATING FILM OF THIN FILM TRANSISTOR

(75) Inventors: Shinichi Maeda, Funabashi (JP); Takahiro Kishioka, Toyama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/131,807

(22) PCT Filed: Nov. 26, 2009

(86) PCT No.: PCT/JP2009/069943
§ 371 (c)(1),
(2), (4) Date: May 27, 2011

(87) PCT Pub. No.: WO2010/061883
PCT Pub. Date: Jun. 3, 2010

(65) Prior Publication Data
US 2011/0227056 A1    Sep. 22, 2011

(30) Foreign Application Priority Data
Nov. 28, 2008   (JP) ................. 2008-304765

(51) Int. Cl.
*H01L 29/08* (2006.01)
*H01L 35/24* (2006.01)
*H01L 51/00* (2006.01)
*H01L 31/062* (2012.01)
*H01L 27/146* (2006.01)

(52) U.S. Cl.
USPC .............. 257/40; 257/291; 257/292; 257/443

(58) Field of Classification Search
USPC ........... 257/40, 324, 410, 411, 223, 227, 291, 257/292, 439, 443, 655
See application file for complete search history.

(56) References Cited

U.S. PATENT DOCUMENTS

| | | | |
|---|---|---|---|
| 7,790,356 B2 | 9/2010 | Kishioka et al. | |
| 2006/0290429 A1 | 12/2006 | Kishioka et al. | |
| 2007/0184365 A1* | 8/2007 | Kim | 430/7 |
| 2008/0038678 A1* | 2/2008 | Kishioka et al. | 430/327 |
| 2008/0206680 A1* | 8/2008 | Kishioka et al. | 430/313 |
| 2009/0114908 A1* | 5/2009 | Hirai et al. | 257/40 |

FOREIGN PATENT DOCUMENTS

| | | |
|---|---|---|
| JP | A-2007-027524 | 2/2007 |
| WO | WO 2004/034148 A1 | 4/2004 |

OTHER PUBLICATIONS

Veres et al., "Gate Insulators in Organic Field-Effect Transistors," *Chem. Mater.*, 2004, vol. 16, pp. 4543-4555.

Kato et al., "High mobility of pentacene field-effect transistors with polyimide gate dielectric layers," *Applied Physics Letters*, 2004, vol. 84, No. 19, pp. 3789-3791.

(Continued)

*Primary Examiner* — Chuong A. Luu
(74) *Attorney, Agent, or Firm* — Oliff PLC

(57) ABSTRACT

It is an object to provide a novel forming agent for a gate insulating film that not only provides high insulating properties for the gate insulating film but also takes account of the electric characteristics of a thin film transistor element. A forming agent for a gate insulating film of a thin film transistor characterized by comprising an oligomer compound or a polymer compound including a structural unit containing a pyrimidinetrione ring having a hydroxyalkyl-containing group as a substituent on a nitrogen atom; a gate insulating film formed by the forming agent; and a thin film transistor.

6 Claims, 1 Drawing Sheet

(56) References Cited

OTHER PUBLICATIONS

Hoshino et al., "Influence of moisture on device characteristics of polythiophene-based field-effect transistors," *Journal of Applied Physics*, 2004, vol. 95, No. 9, pp. 5088-5093.

International Search Report issued in International Application No. PCT/JP2009/069943 dated Mar. 2, 2010.

U.S. Appl. No. 11/547,001.

* cited by examiner

US 8,710,491 B2

FORMING AGENT FOR GATE INSULATING FILM OF THIN FILM TRANSISTOR

TECHNICAL FIELD

The present invention relates to forming agents for gate insulating films of thin film transistors that form gate insulating films having excellent insulating properties and further relates to gate insulating films obtained by using the forming agents and thin film transistors produced using the gate insulating films.

BACKGROUND ART

Currently, various organic materials such as polyimide, acrylic, and polyvinyl phenol are studied, from which gate insulating films of thin film transistors can be formed by application. Such organic materials are practically used in various fields for insulating film materials except for the gate insulating films and can be usually used in a form of a film thickness of 1 μm or more. The reason why such organic materials are used as a film having a film thickness of 1 μm or more is that a film having a larger thickness can reduce leak current as well as increase insulating breakdown voltage. Furthermore, a large film thickness is preferable from the viewpoint of parasitic capacitance reduction in a device.

In contrast, a gate insulating film of an organic transistor is the insulating film for inducing charge in an organic semiconductor layer. Thus, in order to increase charge density in the organic semiconductor layer, the insulating film preferably has a smaller film thickness. Hence, it is difficult to employ the organic materials described above having a film thickness of 1 μm or more as they are for the material for gate insulating films.

Furthermore, the operation of an organic transistor requires the application of a very high electric field of 1 MV/cm or more to a gate insulating film. Most of electronic devices other than the organic transistor do not require such a high electric field, but the gate insulating film of an organic transistor requires extremely high performance as compared with insulating films for other applications.

Thus, the gate insulating film of an organic transistor requires to have a film thickness of 1 μm or less as well as to satisfy a low leak current density (for example, a volume resistivity of $10^{15}$ Ωcm or more (when 1 MV/cm)) and a high insulating breakdown voltage (1 MV/cm or more).

Moreover, it is known that surface free energy (water contact angle) and polarity of the gate insulating film affect mobility of the organic transistor because the gate insulating film is in contact with an organic semiconductor layer of the organic transistor (Non-patent Document 1). In order to increase the mobility, it is believed that the gate insulating film preferably has a flat surface and a low surface free energy. However, the gate insulating film having a too low surface free energy interferes with the formation of a film of an organic semiconductor using a coating solution of an organic semiconductor.

It is further believed that water and oxygen in air also reduce characteristics of the organic transistor (Non-patent Document 2). In addition to the case of the adsorption of water or oxygen into the organic semiconductor layer, water or oxygen may be adsorbed into the gate insulating film. Thus, in order to stabilize an on/off ratio, hygroscopic properties and oxygen adsorption properties of the gate insulating film should be taken into account.

Therefore, material design for the gate insulating film of an organic transistor should be performed in consideration of the characteristics of the organic transistor along with the basic performance of the insulating film. Thus, it is difficult to use an existing insulating film material without any modification.

Furthermore, the most serious problem in the practical use of the organic transistor is heat resistance of a plastic substrate. That is comparatively cheap plastic substrates such as PEN (polyethylene naphthalate) and PET (polyethylene terephthalate) have low heat resistance, and thus other members such as gate insulating films that are formed on the plastic substrate have a limited baking temperature due to the low heat resistance of the plastic substrate. On this account, for example, Non-patent Document 3 discloses a polyimide precursor to be cured at low temperature. However, the polyimide precursor can be dissolved only in some limited solvents such as amide solvents. Therefore, the polyimide precursor is not considered as a insulating film forming material that is soluble in a wide variety of solvents.

DISCLOSURE OF THE INVENTION

Problem to be Solved by the Invention

As discussed above, there has been a demand for a insulating material capable of producing a gate insulating film that can be formed at a comparatively low temperature, for example 180° C. or less, in a coating process and that has basic performance of the insulating film, such as a volume resistivity of $10^{15}$ Ωcm or more, a insulating breakdown voltage of 1 MV/cm or more (in a film having a film thickness of 1 μm or less), high mobility of an organic transistor, a high on/off ratio, and small variation in threshold voltage with, time. However, there is still room for improvement in conventional insulating materials.

There has been another demand for the insulating material that satisfies not only the insulating characteristics of the gate insulating film but also various characteristics of the thin film transistor, for example, high reliability of a thin film transistor in the application of the insulating film to the thin film transistor.

In addition to such electric characteristics of the insulating material, such insulating material has been required to have excellent material usability, that is, required to have high solubility in solvents in general and to readily form a gate insulating film.

In view of the above, it is an object of the present invention to provide a novel forming agent for a gate insulating film that not only provides high insulating properties for the gate insulating film but also takes account of the electric characteristics of a thin film transistor element as well as of the solubility in a solvent, from the viewpoint of practical use.

Means for Solving the Problem

The inventors of the present invention have carried out intensive studies in order to solve the above-mentioned problem. As a result, the inventors have found that, when a cured film is formed from a compound that includes a particular structural unit having a pyrimidinetrione ring and has high solubility, a gate insulating film is easy to be formed, and the formed gate insulating film has high insulating properties. The inventors have also found that a thin film transistor produced using the gate insulating film provides favorable organic transistor characteristics.

Specifically, as a first aspect, the present invention relates to a forming agent for a gate insulating film of a thin film transistor characterized by including an oligomer compound or a polymer compound that includes a structural unit containing a pyrimidinetrione ring having a hydroxyalkyl-containing group as a substituent on a nitrogen atom.

As a second aspect, the present invention relates to the forming agent for a gate insulating film of a thin film transistor according to the first aspect, in which the oligomer compound or the polymer compound is a compound containing a structural unit of Formula [1]:

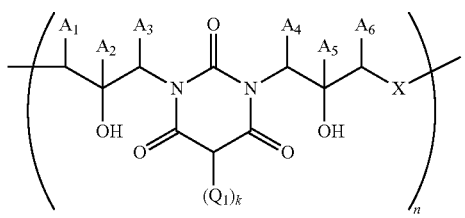

[1]

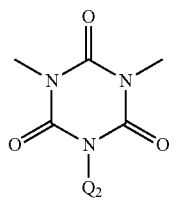

[2]

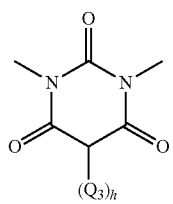

[3]

(where X is a structural unit of Formula [2] or Formula [3], each of $Q_1$, $Q_2$, and $Q_3$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group; each of $A_1$ to $A_6$ is independently a hydrogen atom, a methyl group, or an ethyl group; n is an integer of 1 to 500; and each of k and h is independently 1 or 2).

As a third aspect, the present invention relates to the forming agent for a gate insulating film of a thin film transistor according to the first aspect or the second aspect, in which the oligomer compound or the polymer compound is a reaction product of a compound of Formula [4] and at least one compound selected from compounds of Formula [5] and Formula [6]:

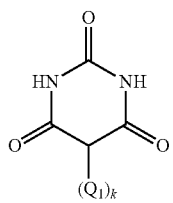

[4]

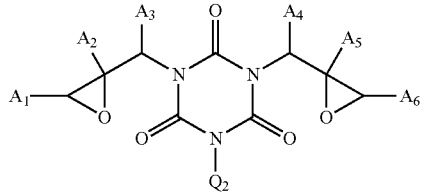

[5]

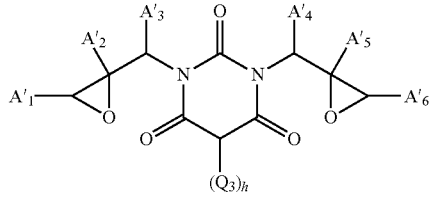

[6]

(where each of $Q_1$, $Q_2$, and $Q_3$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group; each of $A_1$ to $A_6$ and $A'_1$ to $A'_6$ is independently a hydrogen atom, a methyl group, or an ethyl group; and each of k and h is independently 1 or 2).

As a fourth aspect, the present invention relates to a gate insulating film formed by using the forming agent for a gate insulating film of a thin film transistor as described in any one of the first aspect to the third aspect.

As a fifth aspect, the present invention relates to a thin film transistor including the gate insulating film as described in the fourth aspect.

As a sixth aspect, the present invention relates to a method for producing a gate insulating film of a thin film transistor including applying the forming agent for a gate insulating film of a thin film transistor as described in any one of the first aspect to the third aspect to a substrate, and baking the substrate at a temperature of 180° C. or less.

As a seventh aspect, the present invention relates to a method for producing a thin film transistor including producing a gate insulating film of a thin film transistor by applying the forming agent for a gate insulating film of a thin film transistor as described in any one of the first aspect to the third aspect to a substrate and then by baking the substrate at a temperature of 180° C. or less, and forming a semiconductor layer of a thin film transistor by applying an organic semiconductor.

Effects of the Invention

With the forming agent for a gate insulating film of a thin film transistor of the present invention, a film can be formed by a coating method and a gate insulating film can be prepared at a baking temperature of 180° C. or less.

The forming agent for a gate insulating film of a thin film transistor of the present invention is easily dissolved in various solvents, namely, has high solvent solubility, and provides easy control of a solid concentration. Therefore, a gate insulating film having a suitable film thickness can readily be formed.

The gate insulating film of the present invention formed by using the forming agent for a gate insulating film of a thin film transistor satisfies a level of the insulating properties required for the gate insulating film and keeps a leak current of the gate low.

In the gate insulating film of the present invention, a compound constituting the film has an imide skeleton. Hence, the film has higher insulating breakdown voltage than conventional insulating films and the like that are mainly composed of an acrylic skeleton, and therefore has higher reliability as a gate insulating film of a thin film transistor of which a gate insulating film is required to be subjected to a high electric field.

The thin film transistor having the gate insulating am of the present invention can provide an organic thin film transistor that has a low leak current between a source and a drain, a large on/off ratio, a high field-effect mobility, and a small threshold voltage shift, and can maintain such electric characteristics over a long period.

BEST MODES FOR CARRYING OUT THE INVENTION

Hereinafter, the present invention will be described in further detail.

The forming agent for a gate insulating film of a thin film transistor of the present invention includes an oligomer compound or a polymer compound (hereinafter, also called a particular polymer) that includes a structural unit containing a pyrimidinetrione ring having a hydroxyalkyl-containing group as a substituent on a nitrogen atom, includes a solvent as desired, and further includes optional components such as a cross-linking agent, a cross-linking catalyst, a surfactant, and a coupling agent.

[Particular Polymer]

The particular polymer used in the present invention is an oligomer compound or a polymer compound that includes a structural unit containing a pyrimidinetrione ring having a hydroxyalkyl-containing group as a substituent on a nitrogen atom, and is preferably a compound including a structural unit of Formula [1].

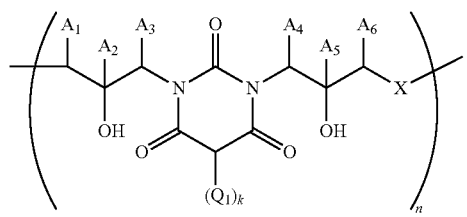

[1]

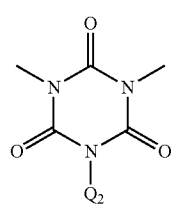

[2]

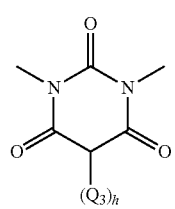

[3]

In Formulae above, X is a structural unit of Formula [2] or Formula [3], and each of $Q_1$, $Q_2$, and $Q_3$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group.

Each of $A_1$ to $A_6$ and $A'_1$ to $A'_6$ is independently a hydrogen atom, a methyl group, or an ethyl group.

n is an integer of 1 to 500, and each of k and h is independently 1 or 2.

In Formulae above, when k or h is 2, each of $Q_1$s and $Q_3$s may be independently the same or different.

Examples of the $C_{1-6}$ alkyl group include a methyl group, an ethyl group, an n-pentyl group, an isopropyl group, an isobutyl group, an isopentyl group, a 1-methylbutyl group, a 1-methylpentyl group, and a cyclohexyl group.

Examples of the $C_{3-6}$ alkenyl group include an allyl group, a 2-butenyl group, a 3-butenyl group, and a 2-pentenyl group.

Examples of the $C_{1-6}$ alkoxy group include a methoxy group, an ethoxy group, an n-propoxy group, an isopropoxy group, an allyloxy group, an n-butoxy group, an isobutoxy group, a sec-butoxy group, a tert-butoxy group, a pentyloxy group, and a hexyloxy group.

Examples of the $C_{1-6}$ alkoxycarbonyl group include a methoxycarbonyl group, an ethoxycarbonyl group, an n-propoxycarbonyl group, an isopropoxycarbonyl group, an n-butoxycarbonyl group, a tert-butoxycarbonyl group, a sec-butoxycarbonyl group, a pentyloxycarbonyl group, a cyclopentyloxycarbonyl group, a hexyloxycarbonyl group, and a cyclohexyloxycarbonyl group.

In each structural unit of Formulae [1] to [3], each of the substituents of $Q_1$, $Q_2$, and $Q_3$ is preferably an alkyl group, an alkenyl group, a fluoroalkyl group, or an alicyclic group such as cyclohexane because the particular polymer obtains high insulating properties.

The molecular weight of the particular polymer is not specifically However, a too low molecular weight leads to a too high solvent solubility, and thus the forming agent may not endure the production process of a transistor. Conversely, a too high molecular weight leads to a too low solvent solubility, and thus the forming agent for a gate insulating film of a thin film transistor having a high concentration may not be obtained. Therefore, the suitable molecular weight is, for example, a weight average molecular weight (in terms of polystyrene) of 1,000 to 200,000 and more preferably 5,000 to 50,000.

The method for obtaining the particular polymer is not specifically limited. For example, the particular polymer can be obtained by polycondensation reaction of a compound of Formula [4] with at least one compound selected from compounds of Formula [5] and Formula [6] in a suitable organic solvent.

For the reaction, each of the compounds of Formula [4], Formula [5], and Formula [6] may be alone or a plurality of compounds.

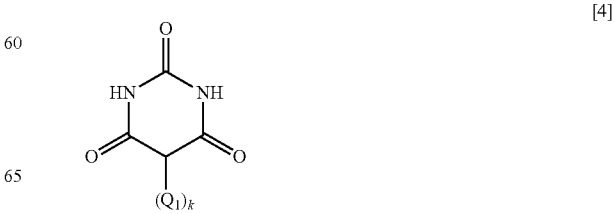

[4]

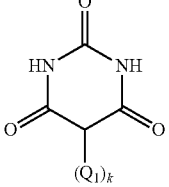

[5]

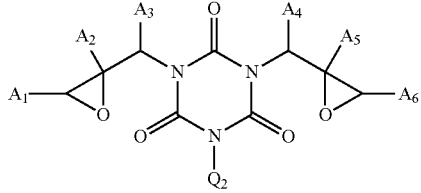

[6]

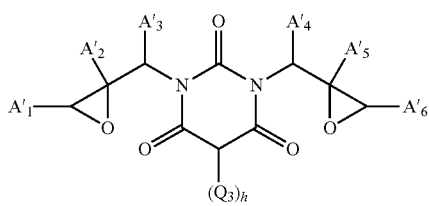

In Formulae above, each of $Q_1$, $Q_2$, and $Q_3$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group.

Each of $A_1$ to $A_6$ and $A'_1$ to $A'_6$ is independently a hydrogen atom, a methyl group, or an ethyl group.

Each of k and h is independently 1 or 2.

Suitable specific examples of the compound of Formula [4] include compounds of Formulae (B-1) to (B-8). Among them, the compounds of Formulae (B-1) to (B-6) are more preferable because such compounds readily produce a particular polymer having high insulating properties.

(B-1)

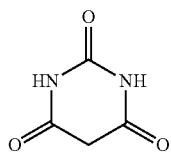

(B-2)

(B-3)

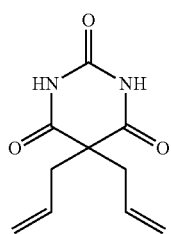

(B-4)

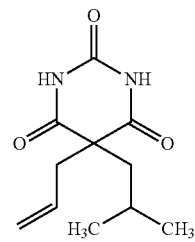

(B-5)

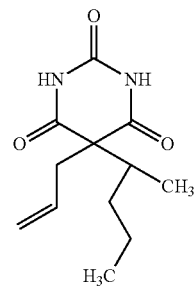

(B-6)

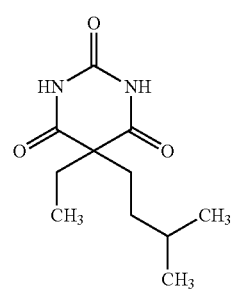

(B-7)

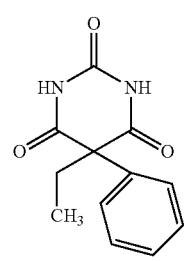

(B-8)

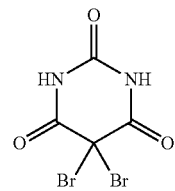

Suitable examples of the compound of Formula [5] include compounds of Formulae (A-1) to (A-11). Among them, the compounds of Formulae (A-1) to (A-9) are more preferable because such compounds readily produce a particular polymer having high insulating properties.

(A-1) 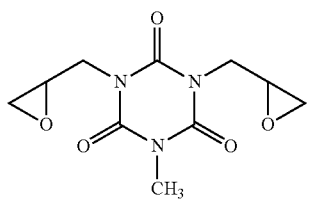
(A-2) 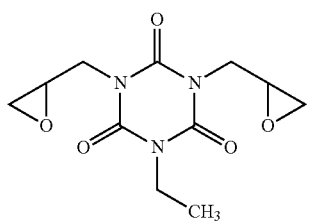
(A-3) 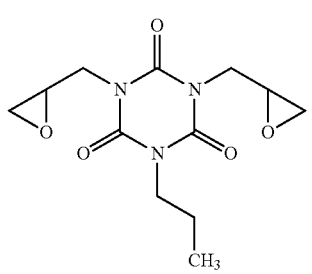
(A-4) 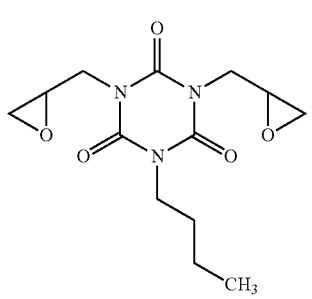
(A-5) 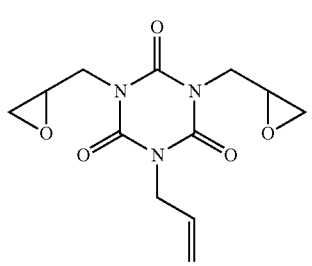
(A-6) 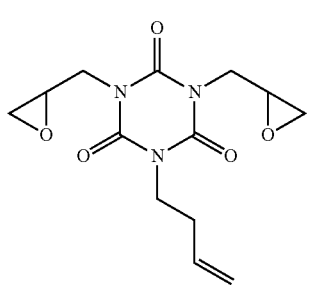
-continued
(A-7) 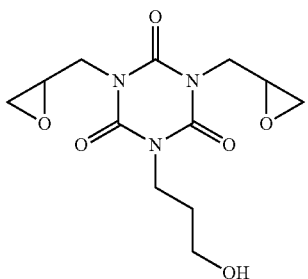
(A-8) 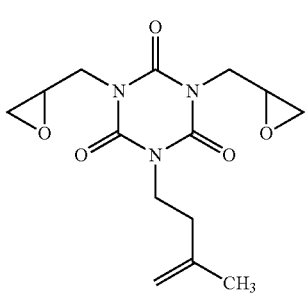
(A-9) 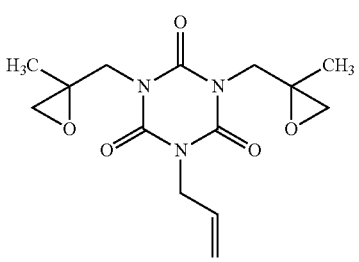
(A-10) 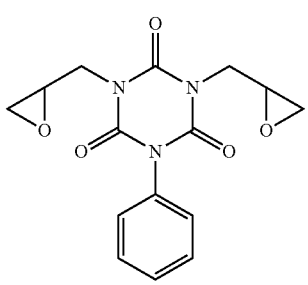
(A-11) 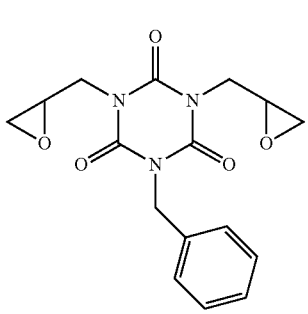

Suitable examples of the compound of Formula [6] include compounds of Formulae (C-1) to (C-8).

(C-1)
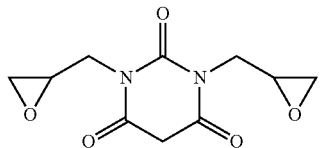

(C-2)
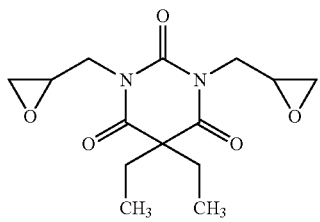

(C-3)
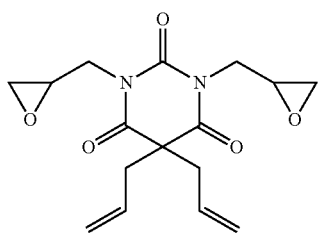

(C-4)
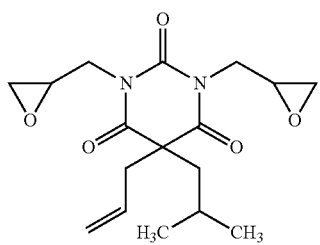

(C-5)
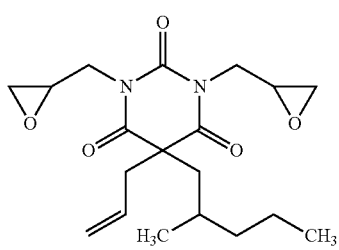

(C-6)
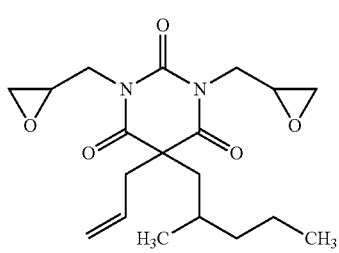

(C-7)
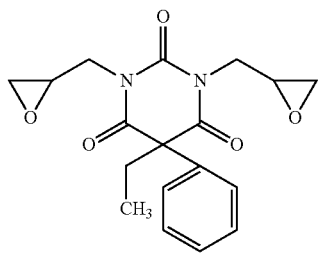

(C-8)
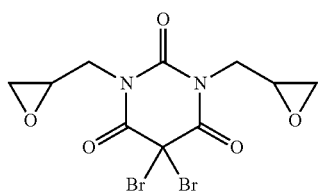

For the method for obtaining the particular polymer, typically, the compound of Formula [4] and at least one compound selected from the compounds of Formula [5] and Formula [6] are mixed in an organic solvent to be subjected to a polycondensation reaction. More specifically, the compound of Formula [4] and at least one compound selected from Formula [5] and Formula [6] are dispersed or dissolved in an organic solvent, and the solution is heated and stirred for reaction. During the reaction, a catalyst may be used.

When plural types of compounds of Formula [4] and plural types of compounds of Formula [5] and/or plural types of compounds of Formula [6] are used, such a plurality of compounds may be mixed to be subjected to a polycondensation reaction, or may be subjected to sequential polycondensation reactions individually.

In the polycondensation reaction, the compounding ratio of the compound of Formula [4] and at least one compound selected from the compounds of Formula [5] and Formula [6], namely, the number of moles of the compound of Formula [4]: the number of moles of at least one compound selected from the compounds of Formula [5] and Formula [6] is desirably 0.5:1 to 1.5:1.

As with common polycondensation reaction, a molar ratio closer to 1:1 increases the polymerization degree of a product to increase the molecular weight.

Examples of the organic solvent used in the polycondensation reaction include ethyl lactate, butyl lactate, propylene glycol monomethyl ether, propylene glycol monomethyl ether acetate, N,N-dimethylformamide, N,N-dimethylformacetamide, N-methyl-2-pyrrolidone, N-methylcaprolactam, dimethyl sulfoxide, tetramethylurea, pyridine, dimethyl sulfone, hexamethyl sulfoxide, γ-butyrolactone, ethylene glycol monomethyl ether, ethylene glycol monoethyl ether, methyl cellosolve acetate, ethyl cellosolve acetate, diethylene glycol monomethyl ether, diethylene glycol monoethyl ether, propylene glycol, propylene glycol propyl ether acetate, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, and butyl acetate.

Examples of the catalyst suitably used in the polycondensation reaction include quaternary ammonium salts such as benzyltriethylammonium chloride, tetrabutylammonium chloride, and tetraethylammonium bromide; and phosphonium salts such as triphenylphosphine, ethyltriphenylphosphonium bromide, and tetrabutylphosphonium bromide.

Such a catalyst as the quaternary ammonium salts and the phosphonium salts is preferably used in a range from 0.001 to 50% by mass with respect to the total mass of the reactants (that is, the compound of Formula [4] and at least one compound selected from the compounds of Formula [5] and Formula [6]).

The reaction temperature and the reaction time of the polycondensation reaction depend on a compound to be used, the concentration of a compound, and the like, and for example, the reaction time is suitably selected from a range of 0.1 to 100 hours, and the reaction temperature is suitably selected from a range of 20° C. to 200° C.

The reaction solution obtained as above may be used as the forming agent for a gate insulating film of a thin film transistor without treatment. However, because the reaction solution includes a catalyst, unreacted monomers, and the like, the reaction product is preferably purified and then used as the forming agent for a gate insulating film.

The reaction product is simply purified by a method of pouring the reaction solution into a poor solvent with stirring to precipitate the reaction product and then filtering the precipitate. Examples of the poor solvent for the purification include, but are not specifically limited to, methanol, hexane, heptane, ethanol, toluene, water, and ether. After filtering the precipitate, the reaction product is preferably washed with the poor solvent. Then, the reaction product may be dried under ambient pressure or reduced pressure at ambient temperature or with heat to turn the reaction product into a powdery form.

The powdery reaction product may further be dissolved in a good solvent and reprecipitated from the poor solvent. Such operation is repeated twice to ten times, and consequently impurities in the reaction product can be further reduced. The usage of three or more poor solvents such as alcohols, ketones, and hydrocarbons for such purification further improves the purification efficiency.

[End Block]

In the polymerization reaction, an end-capping agent may be used in order to improve heat resistance and solvent solubility. A usable end-capping agent is a compound that has reactivity with end groups (an imide group and an epoxy group) in the reaction product of the compound of Formula [4] and at least one compound selected from the compounds of Formula [5] and Formula [6].

When the end group of the particular polymer is an imide group, examples of compounds having reactivity with the imide group include various epoxy compounds, halides, and isocyanates.

In particular, from the viewpoint of transparency, heat resistance, insulating properties, and the like, a compound of Formula [7] is preferred.

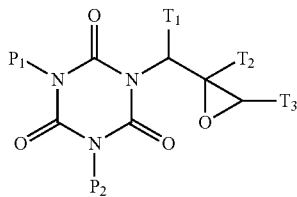

[7]

In the formula, each of $P_1$ and $P_2$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group, and each of $T_1$, $T_2$, and $T_3$ is independently a hydrogen atom, a methyl group, or an ethyl group.

When the end of the particular polymer is an epoxy group, examples of usable compounds having reactivity with, the epoxy group include imides, isocyanuric acid, carboxylic acids, isocyanates, amines, acid anhydrides, halides, esters, and alcohols. Among them, imides, isocyanuric acid, carboxylic acids, isocyanates, and amines are preferred because of ease of handling.

In particular, from the viewpoint of transparency, heat resistance, insulating properties, and the like, a compound of Formula [8] is preferred.

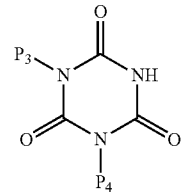

[8]

In the formula, each of $P_3$ and $P_4$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group.

[Solvent]

The forming agent for a gate insulating film of a thin film transistor of the present invention include the particular polymer, a solvent as desired, and other additives described later as desired. Many of the forming agents are usually used in the form of a coating solution dissolved in a solvent.

In the solution, the solid content is, for example, 0.5 to 30% by mass and for example, 5 to 30% by mass. The solid content here means the mass that is obtained by subtracting the mass of a solvent from that of the forming agent for a gate insulating film of a thin film transistor.

When the forming agent is used in the form of a coating solution, examples of the solvent to be used include ethylene glycol monomethyl ether, ethylene glycol monoethyl ether, ethylene glycol monobutyl ether, methyl cellosolve acetate, ethyl cellosolve acetate, diethylene glycol monomethyl ether, diethylene glycol monoethyl ether, propylene glycol, propylene glycol monomethyl ether, propylene glycol monomethyl ether acetate, propylene glycol propyl ether acetate, propylene glycol monobutyl ether, propylene glycol monobutyl ether acetate, dipropylene glycol monomethyl ether, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, lactic acid methyl ester, lactic acid ethyl ester, lactic acid n-propyl ester, lactic acid n-butyl ester, lactic acid isoamyl ester, N,N-dimethylformamide, N,N-dimethylformacetamide, N-methyl-2-pyrrolidone, N-methylcaprolactam, dimethyl sulfoxide, tetramethylurea, pyridine, dimethyl sulfone, hexamethyl sulfoxide, and γ-butyrolactone.

A solvent to be used is suitably selected from these solvents depending on the molecular weight of the oligomer compound or the polymer compound included in the forming agent for a gate insulating film of a thin film transistor of the present invention. Furthermore, in order to control surface tension of the forming agent or to control wettability of the forming agent to a substrate, a plurality of solvents may be mixed for use.

As described above, after the polycondensation reaction of the compound of Formula [4] and at least one compound selected from Formula [5] and Formula [6], the obtained reaction solution may be used as the forming agent for a gate insulating film of a thin film transistor without treatment. In such case, a solvent added for dilution may be the same solvent as that for the polycondensation reaction or another solvent.

[Other Additives]

<Cross-Linking Agent/Cross-Linking Catalyst>

The forming agent for a gate insulating film of a thin film transistor of the present invention may be cross-linked by heat after applying to a substrate in order to prevent intermixing with a semiconductor material or an electrode material to be overcoated. That is, the forming agent may further include a cross-linking agent and a cross-linking catalyst as long as such additive does not interfere with the effect of the invention.

Examples of the cross-linking agent include a melamine compound or a substituted urea compound having at least two cross-linkable substituents such as a methylol group and a methoxymethyl group, and a polymer compound having an epoxy group. Specific examples of the compound include a methoxymethylated glycoluril and a methoxymethylated melamine, and preferred examples include tetramethoxymethylglycoluril and hexamethoxymethylmelamine. The examples of the compound further include tetramethoxymethylurea and tetrabutoxymethylurea.

The amount of the cross-linking agent to be added is suitably selected depending on a type of solvent used in the forming agent for a gate insulating film of a thin film transistor, a solution viscosity to be required, and the like. However, the amount is 0.1 to 100 parts by mass, preferably 1 to 60 parts by mass, and more preferably 10 to 40 parts by mass, based on 100 parts by mass of the total mass of the oligomer compound or the polymer compound included in the forming agent for a gate insulating film of a thin film transistor.

These cross-linking agents may accelerate cross-linking reaction by self-condensation due to the function of cross-linking catalyst, and may cause cross-linking reaction with a cross-linkable substituent included in the particular polymer contained in the forming agent for a gate insulating film of a thin film transistor of the present invention, for example, with a hydroxy group in the structural unit of Formula [1].

The forming agent for a gate insulating film of a thin film transistor of the present invention may contain an acid compound as the cross-linking catalyst. Examples of the acid compound include sulfonic acid compounds such as p-toluenesulfonic acid, trifluoromethanesulfonic acid, and pyridinium-p-toluene sulfonate; and carboxylic acid compounds such as salicylic acid, sulfosalicylic acid, citric acid, benzoic acid, and hydroxybenzoic acid.

The examples of the acid compound further include compounds that produce an acid by light or heat, such as an onium salt compound, a sulfonimide compound, and a disulfonyl diazomethane compound.

Examples of the onium salt compound include iodonium salt compounds such as diphenyliodonium hexafluorophosphate, diphenyliodonium trifluoromethanesulfonate, diphenyliodonium nonafluoro-n-butanesulfonate, diphenyliodonium perfluoro-n-octanesulfonate, diphenyliodonium camphorsulfonate, bis(4-tert-butylphenyl)iodonium camphorsulfonate, and bis(4-tert-butylpheny)iodonium trifluoromethanesulfonate; and sulfonium salt compounds such as triphenylsulfonium hexafluoroantimonate, triphenylsulfonium nonafluoro-n-butanesulfonate, triphenylsulfonium camphorsulfonate, and triphenylsulfonium trifluoromethanesulfonate.

Examples of the sulfonimide compound include N-(trifluoromethanesulfonyloxy)succinimide, N-(nonafluoro-n-butanesulfonyloxy)succinimide, N-(camphorsulfonyloxy) succinimide, and N-(trifluoromethanesulfonyloxy) naphthalimide.

Examples of the disulfonyl diazomethane compound include bis(trifluoromethylsulfonyl)diazomethane, bis(cyclohexylsulfonyl)diazomethane, bis(phenylsulfonyl)diazomethane, bis(p-toluenesulfonyl)diazomethane, bis(2,4-dimethylbenzenesulfonyl)diazomethane, and methylsulfonyl-p-toluenesulfonyldiazomethane.

Examples of the compound producing an acid by light or heat include sulfonic acid ester compounds such as benzoin tosylate, pyrogallol methanesulfonic acid triester, and nitrobenzyl-9,10-diethoxyanthracene-2-sulfonate; and halogen compounds such as phenyl-bis(trichloromethyl)-s-triazine.

These acid compounds may be used singly or in combination of two or more of them.

The amount of the cross-linking catalyst to be added varies depending on a type of solvent used in the forming agent for a gate insulating film of a thin film transistor, a solution viscosity to be required, and the like. However, the amount is 0.01 to 25 parts by mass, preferably 0.1 to 5 parts by mass, and more preferably 0.1 to 2.5 parts by mass, based on 100 parts by mass of the total mass of the oligomer compound or the polymer compound included in the forming agent for a gate insulating film of a thin film transistor.

<Surfactant>

The forming agent for a gate insulating film of a thin film transistor of the present invention may include surfactants in order to suppress the occurrence of pinholes, striations, or the like and to further improve coating properties with respect to surface irregularity.

Examples of the surfactant include nonionic surfactants including polyoxyethylene alkyl ethers such as polyoxyethylene lauryl ether, polyoxyethylene stearyl ether, polyoxyethylene cetyl ether, and polyoxyethylene oleyl ether; polyoxyethylene alkylaryl ethers such as polyoxyethylene octylphenol ether and polyoxyethylene nonylphenol ether; polyoxyethylene-polyoxypropylene block copolymers; sorbitan fatty acid esters such as sorbitan monolaurate, sorbitan monopalmitate, sorbitan monostearate, sorbitan monooleate, sorbitan trioleate, and sorbitan tristearate; and polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine-based surfactants including trade name EFTOP EF301, EF303, and EF352 (manufactured by Jemco Inc.), trade name MEGAFAC F171, F173, R-08, and R-30 (manufactured by DIC Corporation (formerly Dainippon Ink and Chemicals, Inc.)), Fluorad FC430 and FC431 (manufactured by Sumitomo 3M Ltd.), and trade name AsahiGuard AG 710 and Surflon S-382, SC101, SC102, SC103, SC104, SC105, and SC106 (manufactured by Asahi Glass Co., Ltd.); and organosiloxane polymer KP341 (manufactured by Shin-Etsu Chemical Co., Ltd.).

The mixing amount of the surfactant is commonly 1% by mass or less and preferably 0.5% by mass or less, with respect to the total solid content of the forming agent for a gate insulating film of a thin film transistor of the present invention. These surfactants may be added singly or in combination of two or more of them.

<Coupling Agent>

The forming agent for a gate insulating film of a thin film transistor of the present invention may further include a coupling agent in order to improve the adhesion between the forming agent and a substrate as long as the coupling agent does not interfere with the effect of the invention. Examples of the coupling agent include functional silane-containing compounds and epoxy group-containing organic compounds.

Specific examples include functional silane-containing compounds such as 3-aminopropyltrimethoxysilane, 3-aminopropylthethoxysilane, 2-aminopropyltrimethoxysilane, 2-aminopropyltriethoxysilane, N-(2-aminoethyl)-3-aminopropyltrimethoxysilane, N-(2-aminoethyl)-3-aminopropylmethyldimethoxysilane, 3-ureidopropyltrimethoxysilane, 3-ureidopropyltriethoxysilane, N-ethoxycarbonyl-3-aminopropyltrimethoxysilane, N-ethoxycarbonyl-3-aminopropyltriethoxysilane, N-trimethoxysilylpropyltriethylenetriamine, N-triethoxysilylpropyltriethylenetriamine, 10-trimethoxysilyl-1,4,7-triazadecane, 10-triethoxysilyl-1,4,7-triazadecane, 9-trimethoxysilyl-3,6-diazanonyl acetate, 9-triethoxysilyl-3,6-diazanonyl acetate, N-benzyl-3-aminopropyltrimethoxysilane, N-benzyl-3-aminopropyltriethoxysilane, N-phenyl-3-aminopropyltrimethoxysilane, N-phenyl-3-aminopropyltriethoxysilane, N-bis(oxyethylene)-3-aminopropyltrimethoxysilane, and N-bis(oxyethylene)-3-aminopropyltriethoxysilane; and epoxy group-containing compounds such as ethylene glycol diglycidyl ether, polyethylene glycol diglycidyl ether, propylene glycol diglycidyl ether, tripropylene glycol diglycidyl ether, polypropylene glycol diglycidyl ether, neopentyl glycol diglycidyl ether, 1,6-hexanediol diglycidyl ether, glycerin diglycidyl ether, 2,2-dibromoneopentyl glycol diglycidyl ether, 6-tetraglycidyl-2,2-hexanediol, N,N,N',N'-tetraglycidyl-m-xylenediamine, 1,3-bis(N,N-diglycidylaminomethyl)cyclohexane, and N,N,N',-tetraglycidyl-4,4'-diaminodiphenylmethane.

The content of the coupling agent to be used is preferably 0.1 to 30 parts by mass and more preferably 1 to 20 parts by mass, based on 100 parts by mass of the oligomer compound or the polymer compound included in the forming agent for a gate insulating film of a thin film transistor.

[Production Method of Coating Film and Cured Film]

The forming agent for a gate insulating film of a thin film transistor of the present invention can form a coating film by applying the forming agent onto a common plastic substrate made from, for example, polypropylene, polyethylene, polycarbonate, polyethylene terephthalate, polyethersulfone, polyethylene naphthalate, and polyimide, a glass substrate, or the like, by a dipping method, a spin coating method, a transfer printing method, a roll coating method, an ink-jetting method, a spraying method, a brush coating method, or the like, and then by predrying the substrate using a hot plate, an oven, or the like.

Next, the coating film is heat treated (baked) to form a cured film that can be used as the gate insulating film.

The heat treatment method is not specifically limited and, for example, can be performed in a suitable atmosphere, for example, in air, in an inert gas such as nitrogen, and in vacuum, using a hot plate or an oven.

The baking temperature is preferably 40° C. or more and more preferably 150° C. or more in order to reduce a residual solvent in the coating film. The baking temperature is desirably 180° C. or less in consideration of the heat resistance of a plastic substrate.

The baking may be carried out in two or more temperature stages. The step-by-step baking increases uniformity of the cured film.

The gate insulating film of the present invention obtained in this manner preferably has a film thickness of 5 nm to 5,000 nm, more preferably 50 nm to 1,000 nm, and most preferably 200 nm to 600 nm. When the gate insulating film is too thin, insulating breakdown occurs in a low electric field so that the gate insulating film does not work as a transistor. When the gate insulating film is too thick, high voltage is required for operating a transistor. Therefore, the gate insulating film is desirably formed to have a film thickness in the range above.

When a desired thickness of the cured film (gate insulating film) is not obtained by a single coating and heat treatment, the process of coating and heat treatment may be repeated until a desired film thickness is obtained.

[Thin Film Transistor]

The constitution of the thin film transistor of the present invention is not specifically limited as long as the gate insulating film of the present invention is used. As examples, FIG. 1 to FIG. 4 show constitution examples of the thin film transistor using the gate insulating film of the present invention.

In the examples in FIG. 1 to FIG. 3, the thin film transistor of the present invention has a substrate 1 on which a gate electrode 2 is formed, and the gate electrode 2 is covered with the gate insulating film 3 (or 3a or 3b) of the present invention.

In the example of FIG. 1, on the gate insulating film 3, a source electrode 4 and a drain electrode 4 are installed, and a semiconductor layer 5 is formed so as to cover the electrodes.

In the example of FIG. 2, on the gate insulating film 3, a semiconductor layer 5 is formed, and a source electrode 4 and a drain electrode 4 are installed on the semiconductor layer 5.

In the example of FIG. 3, on the gate insulating film 3a, a gate insulating film 3b is formed, and a source electrode and a drain electrode are installed on the gate insulating film 3b. A semiconductor layer 5 is formed so as to cover the electrodes. Here, the gate insulating film 3b has the function of a insulating film that controls transistor characteristics as well as the function of a surface treatment film or an underlayer film for forming electrodes with respect to the source electrode 4 and the drain electrode 4.

In the example of FIG. 4, a semiconductor layer 5 is formed on a substrate 1, and a source electrode 4 and a drain electrode 4 are installed so as to cover both the semiconductor layer 5 and the substrate 1. The gate insulating film 3 is formed on the semiconductor layer 5, the source electrode 4, and the drain electrode 4, and a gate electrode 2 is installed on the gate insulating film 3.

Examples of materials for the electrodes (the gate electrode, the source electrode, and the drain electrode) used in the thin film transistor of the present invention include metals such as gold, silver, copper, aluminum, and calcium; inorganic materials such as carbon black, fullerenes, and carbon nanotubes; and organic π-conjugated polymers such as polythiophene, polyaniline, polypyrrole, polyfluorene, and derivatives of them.

These electrode materials may be used singly, or in combination of a plurality of materials in order to improve a field-effect mobility or an on/off ratio of the thin film transistor or in order to control threshold voltage. The electrode materials used for the gate electrode, the source electrode, and the drain electrode may be different to each other.

The method for forming the electrode commonly employs vacuum deposition, sputtering, or the like. However, in order to simplify the production method, coating methods such as a spray coating method, a printing method, and an ink-jetting method have been developed for the forming method of the electrode.

Examples of applicable electrode materials include metal nanoparticles and organic π-conjugated polymers.

Preferred solvents for a nano metal ink or an organic π-conjugated polymer in the formation of the electrode by coating are water and various alcohols because of low damage (intermixing) to the gate insulating film of the present invention.

Polar solvents such as N,N-dimethylformamide, N,N-dimethylacetamide, 2-pyrrolidone, N-methyl-2-pyrrolidone, n-ethyl-2-pyrrolidone, n-vinyl-2-pyrrolidone, N-methylcaprolactam, dimethyl sulfoxide, and tetramethylurea are also preferred from the viewpoint of an excellent solubility of an electrode material. Such solvent is preferably used in a range where low damage is caused to the gate insulating film of the present invention.

A material used for the semiconductor layer included in the thin film transistor of the present invention is not specifically limited as long as the semiconductor layer can be formed on the gate insulating film of the present invention, on the electrode, and on the plastic substrate. Specific examples of the material include organic low molecular materials such as pentacene, oligothiophene derivatives, and phthalocyanine derivatives; π-conjugated polymers such as polythiophene derivatives, polyphenylene vinylene derivatives, and polyfluorene derivatives; and oxide semiconductors such as InGaZnO-based, InGaO-based, ZnGaO-based, InZnO-based, ZnO, and $SnO_2$.

Such semiconductor material may be formed into a film by a film forming method such as a sputtering method, a vacuum deposition method, an ink-jetting method, and a spraying method. In particular, coating methods such as an ink-jetting method and a spraying method are preferred because such methods are simple and can reduce the production cost.

Examples of the semiconductor material suitable for the coating method include π-conjugated polymers that have a high solvent solubility and readily form a uniform thin film.

A solvent of the π-conjugated polymer for the film formation is not specifically limited as long as the polymer can be dissolved or uniformly dispersed and the gate insulating film of the present invention is less damaged (for example, less intermixing). Examples of specifically preferred solvents include aromatic hydrocarbon solvents such as toluene, xylene, and mesitylene.

EXAMPLES

Hereinafter, the present invention will be described in detail with reference to examples, but the present invention is not limited to them.

[Determination of Number Average Molecular Weight and Weight Average Molecular Weight]

In Examples, each molecular weight of P-1, P-2, and P-3 that were obtained by polymerization was measured with a GPC (ambient temperature gel permeation chromatography) apparatus, and a number average molecular weight and a weight average molecular weight for each product were determined as values in terms of polystyrene.
GPC apparatus: manufactured by JASCO Corporation (JASCO-BORWIN Ver. 1.50)
Column: manufactured by Shodex (804 and 805 in series)
Column temperature: 40° C.
Eluant: tetrahydrofuran
Flow rate: 1.0 ml/min
Standard samples for preparing calibration curve: standard polystyrene (210,000, 70,600, 28,600, 10,900, 3,000, and 1,300)

In Examples, the molecular weight of polyamic acid obtained by polymerization was measured with a GPC (ambient temperature gel permeation chromatography) apparatus, and a number average molecular weight and a weight average molecular weight of the polyamic acid was determined as a value in terms of polyethylene glycol or polyethylene oxide.
GPC apparatus: manufactured by Shodex (GPC-101)
Column: manufactured by Shodex (KD803 and KD805 in series)
Column temperature: 50° C.
Eluant: N,N-dimethylformamide (including, as additives, 30 mmol/L lithium bromide monohydrate ($LiBr.H_2O$), 30 mmol/L phosphoric acid anhydrate crystal (O-phosphoric acid), and 10 ml/L tetrahydrofuran (THF))
Flow rate: 1.0 ml/min
Standard samples for preparing calibration curve: standard polyethylene oxide (molecular weight: about 900,000, 150,000, 100,000, and 30,000), and polyethylene glycol manufactured by Polymer Laboratories Ltd. (molecular weight: about 12,000, 4,000, and 1,000)

[Determination of Film Thickness]

Each film thickness was determined by peeling a part of a film with a cutter knife and measuring the step height using a full-automatic fine shape measuring instrument (ET4000A, manufactured by Kosaka Laboratory Ltd.) at a measuring force of 10 μN and a sweep speed of 0.05 mm/sec.

Synthesis Example 1

P-1

Monoallyldiglycidyl isocyanuric acid (100 g), diethylbarbituric acid (66.4 g), and benzyltriethylammonium chloride (4.1 g) were dissolved in propylene glycol monomethyl ether (682 g) and then reacted at 130° C. for 24 hours to give a polymer compound solution.

The obtained polymer compound was added dropwise into a methanol solvent, and the precipitate was filtered to give a reaction product P-1 (white powder).

The reaction product P-1 was subjected to GPC analysis to give a weight average molecular weight (Mw) of 9,970 in terms of standard polystyrene.

The reaction product P-1 obtained in this synthesis example had a structural unit of Formula [S-1].

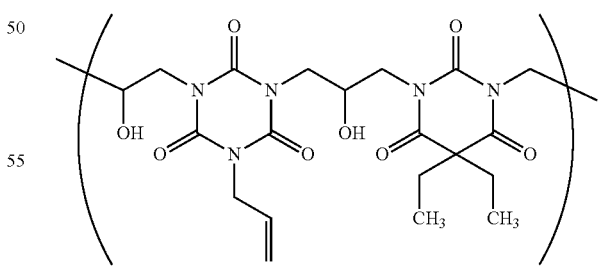

Synthesis Example 2

Synthesis of P-2

In propylene glycol monomethyl ether (682 g), 1,3-diglycidyl-5,5-diethylpyrimidinetrione (100 g), diethylbarbituric acid (66.4 g), and benzyltriethylammonium chloride (4.1 g) were dissolved and then reacted at 130° C. for 24 hours to give a polymer compound solution.

The obtained polymer compound was added dropwise into a methanol solvent, and the precipitate was filtered to give a reaction product P-2 (white powder).

The reaction product P-2 was subjected to GPC analysis to give a weight average molecular weight (Mw) of 3,300 in terms of standard polystyrene.

The reaction product P-2 obtained in this synthesis example had a structural unit of Formula [S-2].

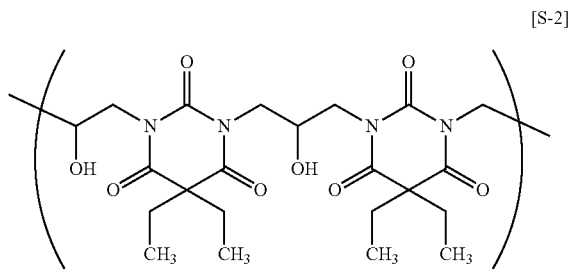

[S-2]

Synthesis Example 3

P-3

Monoallyldiglycidyl isocyanuric acid (100 g), 5-ethyl-5-phenylbarbituric acid (66.4 g), and benzyltriethylammonium chloride (4.1 g) were dissolved in propylene glycol monomethyl ether (682 g) and then reacted at 130° C. for 24 hours to give a polymer compound solution.

The obtained polymer compound was added dropwise into a methanol solvent, and the precipitate was filtered to give a reaction product P-3 (white powder).

The reaction product P-3 was subjected to GPC analysis to give a weight average molecular weight (Mw) of 12,400 in terms of standard polystyrene.

The reaction product P-3 obtained in this synthesis example had a structural unit of Formula [S-3].

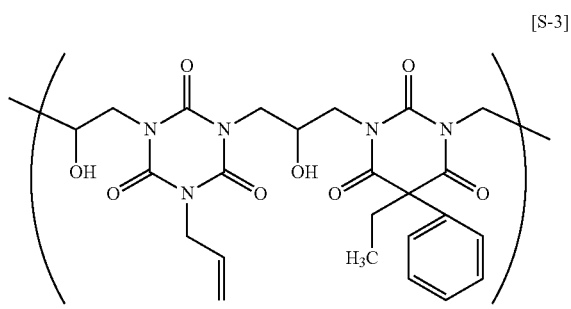

[S-3]

Comparative Synthesis Example 1

Under a stream of nitrogen, 8.01 g (0.040 mol) of 4,4'-diaminodiphenyl ether was placed in a 200-mL 4-necked flask and dissolved with 91.9 g of N-methyl-2-pyrrolidone (NMP). Then, 8.20 g (0.038 mol) of pyromellitic dianhydride was added, and the whole was stirred at 23° C. for 2 hours for polymerization reaction and then diluted with NMP to give a 6% by weight polyamic acid solution.

The obtained polyamic acid had a weight average molecular weight (Mw) of 25,200.

[Preparation of Forming Agent for Gate Insulating Film of Thin Film Transistor]

Example 1

Preparation of Forming Agent A

In a mixed solvent of propylene glycol monomethyl ether (PGME) and propylene glycol monomethyl ether acetate (PGMEA) (7:3), 10 g of P-1 (white powder) obtained in Synthesis Example 1 was dissolved, and then 0.03 g of MEGAFAC R-30 (manufactured by DIC Corporation) was added as a surfactant to give a forming agent A having a solid concentration of 13% by mass.

Example 2

Preparation of Forming Agent B

In a mixed solvent of PGME and PGMEA (7:3), 2.1 g of P-2 (white powder) obtained in Synthesis Example 2 was dissolved, and then 0.006 g of MEGAFAC R-30 (manufactured by DIC) was added as a surfactant to give a forming agent B having a solid concentration of 20% by mass.

Example 3

Preparation of Forming Agent C

In a mixed solvent of PGME and PGMEA (7:3), 2.1 g of P-2 (white powder) obtained in Synthesis Example 2 was dissolved, and then 0.006 g of MEGAFAC R-30 (manufactured by DIC) as a surfactant, 0.53 g of tetramethoxymethylglycoluril (product name: POWDERLINK 1174, manufactured by CYTEC) as a cross-linking agent, and 0.05 g of pyridinium p-toluenesulfonate as a cross-linking catalyst were added to give a forming agent C having a solid concentration of 20% by mass.

Example 4

Preparation of Forming Agent D

In a mixed solvent of γ-butyrolactone and dipropylene glycol monomethyl ether (DPM) (8:2), 10 g of P-3 (white powder) obtained in Synthesis Example 3 was dissolved to give a forming agent D having a solid concentration of 15% by mass.

[Production of Gate Insulating Film and Electric Characteristic Evaluation of the Insulating Film]

Example 5

Gate Insulating Film Using Forming Agent A

Onto a glass substrate with ITO (2.5 cm per side, a thickness of 0.7 mm), the forming agent A prepared in Example 1 was added dropwise through a syringe installed with a filter having a pore size of 0.2 μm and coated by a spin coating method. Then, the coated substrate was treated with heat (predried) in the atmosphere on a hot plate at 80° C. for 5 minutes to volatilize the organic solvents. Next, the substrate was baked on a hot plate at 180° C. for 60 minutes to give a gate insulating film having a film thickness of 470 nm.

Next, on the gate insulating film, an aluminum electrode having a diameter of 0.5 mm to 1.5 mm and a film thickness of 100 nm was deposited using a vacuum deposition equipment to prepare a sample for evaluating the insulating properties of the gate insulating film that had the electrodes on both sides of the gate insulating film. Here, conditions for the vacuum deposition were at room temperature, a degree of vacuum of $3 \times 10^{-3}$ Pa or less, and an aluminum deposition rate of 0.5 nm/sec or less.

Using the sample, current-voltage characteristics were measured in the atmosphere at room temperature and a humidity of 45%±5%. The voltage was applied to the aluminum electrode while a positive voltage was stepwisely increased by 2 V from 0 V to 80 V with a retention time of 3 seconds per step, and the specific resistance was calculated from the current value at an electric field of 1 MV/cm. The results are shown in Table 1.

Example 6

Gate Insulating Film Using Forming Agent B

Using the forming agent B prepared in Example 2, a gate insulating film was formed on a substrate by the same procedure as in Example 5.

Subsequently, a sample for evaluating the insulating properties was prepared by the same procedure as in Example 5, and the current-voltage characteristics were measured to calculate the specific resistance. The results are shown in Table 1.

Example 7

Gate Insulating Film Using Forming Agent C

Using the forming agent C prepared in Example 3, a gate insulating film was formed on a substrate by the same procedure as in Example 5.

Subsequently, a sample for evaluating the insulating properties was prepared by the same procedure as in Example 5, and the current-voltage characteristics were measured to calculate the specific resistance. The results are shown in Table 1.

Example 8

Gate Insulating Film Using Forming Agent D

Using the forming agent D prepared in Example 4, a gate insulating film was formed on a substrate by the same procedure as in Example 5.

Subsequently, a sample for evaluating the insulating properties was prepared by the same procedure as in Example 5, and the current-voltage characteristics were measured to calculate the specific resistance. The results are shown in Table 1.

Comparative Example 1

Gate Insulating Film Using Polyamic Acid

Using the polyamic acid solution prepared in Comparative Synthesis Example 1, a gate insulating film was formed on a substrate by the same procedure as in Example 5.

Subsequently, a sample for evaluating the insulating properties was prepared by the same procedure as in Example 5, and the current-voltage characteristics were measured to calculate the specific resistance. The results are shown in Table 1.

TABLE 1

| | Electric characteristics of gate insulating film | | | |
|---|---|---|---|---|
| | | Film thickness | Specific resistance/ $\Omega$cm | Relative permittivity |
| Example 5 | Forming agent A | 470 nm | $3.7 \times 10^{16}$ | 3.6 |
| Example 6 | Forming agent B | 400 nm | $1.3 \times 10^{15}$ | 3.6 |
| Example 7 | Forming agent C | 350 nm | $2.4 \times 10^{15}$ | 3.5 |
| Example 8 | Forming agent D | 400 nm | $1.7 \times 10^{15}$ | 3.6 |
| Comparative Example 1 | Polyamic acid | 470 nm | $1.9 \times 10^{13}$ | 3.6 |

As shown in Table 1, each gate insulating film of Example 5 to Example 8 had a specific resistance of $10^{15}$ $\Omega$cm or more, and was revealed to be suitably used for the gate insulating film of a thin film transistor.

[Production of Organic Thin Film Transistor and Electric Characteristic Evaluation of the Transistor]

Example 9

P3HT Organic Thin Film Transistor Using Insulating Film Formed from Forming Agent A Using the forming agent A prepared in Example 1, a gate insulating film was formed on a substrate by the same procedure as in Example 5 except that the film thickness was 400 nm.

The capacitance C of the gate insulating film was 8.0 nF/cm$^2$ by calculating from the relative permittivity and the film thickness of the insulating film.

Next, on the gate insulating film, a semiconductor layer was formed. First, poly(3-hexylthiophene-2,5-diyl) (purchased from Merck & Co., Inc., hereinafter called P3HT) was dissolved in xylene at a concentration of 2% by mass to prepare a P3HT coating solution. The coating solution was applied onto the gate insulating film by a spin coating method under a nitrogen atmosphere having an oxygen concentration of 0.5 ppm or less. Then, for complete volatilization of the solvent, the coated substrate was treated with heat in vacuum at 100° C. for 60 minutes to form a semiconductor layer.

Furthermore, using a vacuum deposition equipment, about 60 nm of gold was deposited on the semiconductor layer (P3HT film) to form source and drain electrodes each having a channel length L of 90 μm and a channel width W of 2 mm so that the production of an organic thin film transistor is completed. The cross-sectional view of the organic thin film transistor shown in FIG. 2 corresponds to the organic thin film transistor of Example 9.

The conditions for the vacuum deposition of the electrodes were at room temperature, a degree of vacuum of $1 \times 10^{-3}$ Pa or less, and a gold deposition rate of 0.1 nm/sec or less.

The electric characteristics in vacuum of the organic thin film transistor obtained as above were evaluated by measurement of change of the drain current with respect to the gate voltage.

In particular, while the soiree/drain voltage ($V_D$) was set at −40 V, the gate voltage ($V_G$) was stepwisely changed by 2 V from +60 V to −40 V. The voltage was kept for 1 second until the current was completely stabilized, and then the drain current was recorded as the measured value. For the measurement, a semiconductor parameter analyzer HP4156C (manufactured by Agilent Technologies, Inc.) was used.

When the gate voltage was negatively applied, the drain current was largely increased, and therefore P3HT was confirmed to work as a p-type semiconductor.

The drain current $I_D$ in a saturated state is usually expressed by the formula below. Thus, the mobility μ of an organic semiconductor can be determined from the slope of the graph in which the square root of the absolute value of the drain current $I_D$ is plotted on the vertical axis and the gate voltage $V_G$ is plotted on the horizontal axis.

$$I_D = WC\mu(V_G - V_T)^2/2L$$

In the formula, W is a channel width of the transistor, L is a channel length of the transistor, C is a capacitance of the gate insulating film, $V_T$ is a threshold voltage of the transistor, and μ is a mobility. The mobility μ of P3HT was $2\times10^{-3}$ cm²/Vs as calculated based on the formula. The threshold voltage was 25 V, and the ratio of on state and of state (on/off ratio) was in the order of $10^2$ (Table 2).

In order to remove the effects of ambient humidity and active substances, the element was transferred into a vacuum system (at a degree of vacuum of $5\times10^{-2}$ Pa or less) immediately after the production of the element is completed and left for about 30 minutes. Then, the electric characteristics of the organic thin film transistor were measured while the degree of vacuum was kept at $5\times10^{-2}$ Pa or less.

Example 10

F8T2 Organic Thin Film Transistor Using Insulating Film Formed from Forming Agent A Using the forming agent A prepared in Example 1, a gate insulating film was formed on a substrate by the same procedure as in Example 5 except that the film thickness was 470 nm.

The capacitance C of the gate insulating film was 6.7 nF/cm² by calculating from the relative permittivity and the film thickness of the insulating film.

Next, on the gate insulating film, a semiconductor layer was formed. First, poly(9,9-dioctylfluorene-alt-bithiophene) (purchased from American Dye Source Inc., hereinafter called F8T2) was dissolved in xylene at a concentration of 1.5% by mass to prepare an F8T2 coating solution. The coating solution was applied onto the gate insulating film by a spin coating method under a nitrogen atmosphere having an oxygen concentration of 0.5 ppm or less. Then, for complete volatilization of the solvent, the coated substrate was treated with heat in vacuum at 135° C. for 60 minutes to form a semiconductor layer.

Furthermore, using a vacuum deposition equipment, about 60 nm of gold was deposited on the semiconductor layer (F8T2 film) to form source and drain electrodes each having a channel length L of 90 μm and a channel width W of 2 mm so that the production of an organic thin film transistor is completed. The cross-sectional view of the organic thin film transistor shown in FIG. 2 corresponds to the organic thin film transistor of Example 10.

The conditions for the vacuum deposition of the electrodes were at room temperature, a degree of vacuum of $1\times10^{-3}$ Pa or less, and a gold deposition rate of 0.1 nm/sec or less.

The electric characteristics in vacuum of the organic thin film transistor obtained as above were evaluated by the same procedure as in Example 10. While the source/drain voltage ($V_D$) was set at −100 V, the gate voltage ($V_G$) was stepwisely changed by 4 V from 0 V to −100 V.

The mobility μ of F8T2 was calculated as $4\times10^{-4}$ cm²/Vs based on the formula above. The threshold voltage was −30 V, and the ratio of on state and off state (on/off ratio) was in the order of $10^4$ (Table 2).

In order to remove the effects of ambient humidity and active substances, the element was transferred into a vacuum system (at a degree of vacuum of $5\times10^{-2}$ Pa or less) immediately after the production of the element is completed, and left for about 30 minutes. Then, the electric characteristics of the organic thin film transistor were measured while the degree of vacuum was kept at $5\times10^{-2}$ Pa or less.

Comparative Example 2

P3HT Organic Thin Film Transistor Using Insulating Film Formed from Polyamic Acid Solution An organic thin film transistor was produced by the same procedure as in Example 9 except that the polyamic acid solution obtained in Comparative Synthesis Example 1 was used and the film thickness was 370 nm.

The capacitance C of the gate insulating film was 8.6 nF/cm² as calculated from the relative permittivity and the film thickness of the insulating film.

The calculated mobility μ of P3HT was $1\times10^{-3}$ cm²/Vs, but the on/off ratio was in the order of $10^1$, and the organic thin film transistor did not work normally (Table 2).

TABLE 2

| | Characteristics of Organic Thin Film Transistor | | | |
|---|---|---|---|---|
| | Semi-conductor layer | Mobility (cm²/Vs) | Threshold voltage (V) | On/off ratio |
| Example 9 | Forming agent A | P3HT | $2 \times 10^{-3}$ | +25 | $10^2$ |
| Example 10 | Forming agent A | F8T2 | $4 \times 10^{-4}$ | −30 | $10^4$ |
| Comparative Example 2 | Polyamic acid solution | P3HT | $1 \times 10^3$ | Undetectable | $10^1$ |

As shown in Table 2, each organic thin film transistor of Example 9 to Example 10 that used the gate insulating film obtained by baking the forming agent A at 180° C. showed favorable transistor characteristics.

DESCRIPTION OF THE REFERENCE NUMERALS

Figure 1:
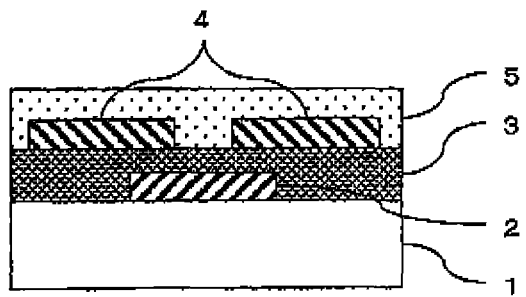
FIG. 1 is a schematic cross-sectional view showing the structure of the thin film transistor of the first example having the gate insulating film of the present invention.
Figure 2:
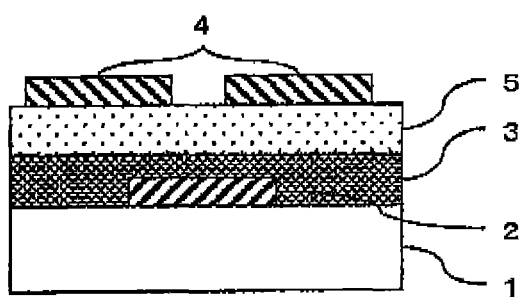
FIG. 2 is a schematic cross-sectional view showing the structure of the thin film transistor of the second example having the gate insulating film of the present invention.
Figure 3:
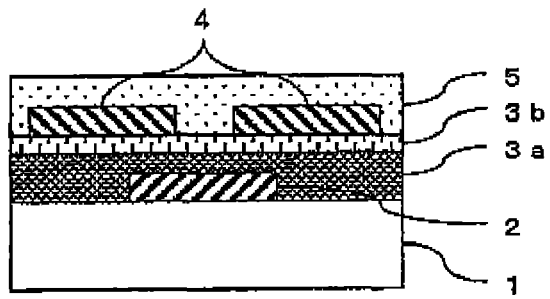
FIG. 3 is a schematic cross-sectional view showing the structure of the thin film transistor of the third example having the gate insulating film of the present invention.
Figure 4:
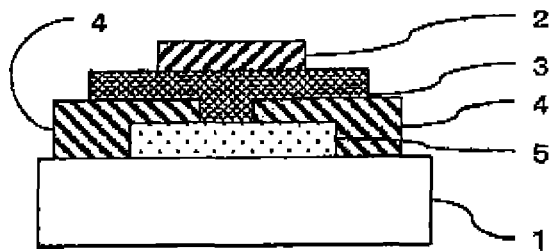
FIG. 4 is a schematic cross-sectional view showing the structure of the thin film transistor of the fourth example having the gate insulating film of the present invention.

1 Substrate
2 Gate electrode
3 (3a, 3b) Gate insulating film

4 Source electrode, drain electrode
5 Semiconductor layer

RELATED ART DOCUMENTS

Non-Patent Documents

Non-patent Document 1: "Chemistry of Materials (Chem. Mater.)", Vol. 16, 2004, pp, 4543-4555.
Non-patent Document 2: "Journal of Applied Physics (J. Appl. Phys.)", Vol. 95, No, 9, 2004, pp. 5088-5093.
Non-patent Document 3; "Applied Physics Letters (Appl. Phys. Lett.)", Vol. 84, No. 19, 10 May 2004, pp. 3789-3791.

The invention claimed is:
1. A thin film transistor comprising:
a substrate;
a gate electrode;
a gate insulating film including a component (i): an oligomer compound or a polymer compound with a repeating unit represented by the following formula [1]:

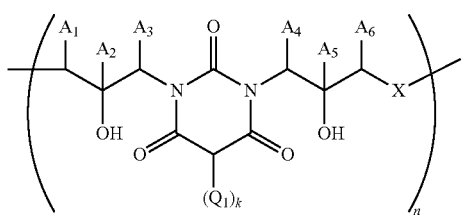

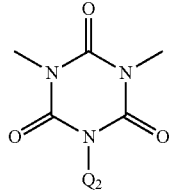

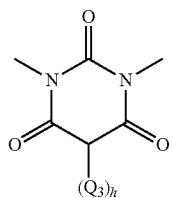

(where X is a structural unit of Formula [2] or Formula [3], each of $Q_1$, $Q_2$, and $Q_3$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group; each of $A_1$ to $A_6$ is independently a hydrogen atom, a methyl group, or an ethyl group; n is an integer of 1 to 500; and each of k and h is independently 1 or 2);
source and drain electrodes; and
a semiconductor layer.

2. The forming agent for a gate insulating film of a thin film transistor according to claim 1 wherein the oligomer compound or the polymer compound is a reaction product of a compound of Formula [4] and at least one compound selected from compounds of Formula [5] and Formula [6]:

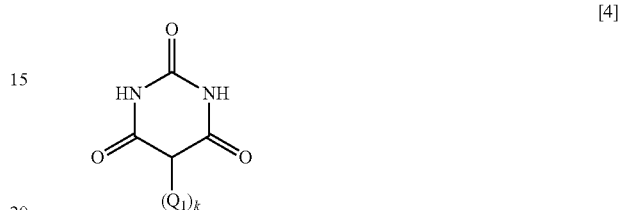

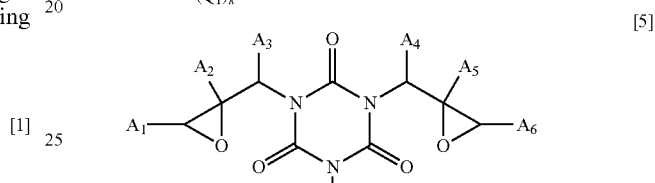

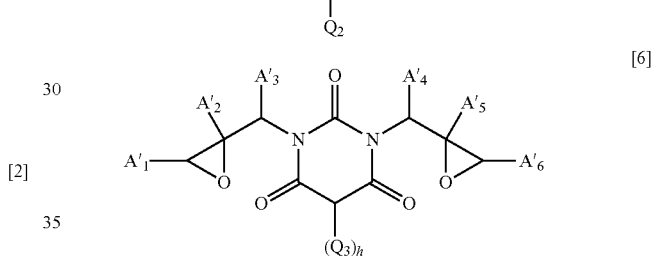

(where each of $Q_1$, $Q_2$, and $Q_3$ is independently a hydrogen atom, an optionally branched $C_{1-6}$ alkyl group, $C_{3-6}$ alkenyl group, $C_{1-6}$ alkoxy group, or $C_{1-6}$ alkoxycarbonyl group, a phenyl group, a trifluoromethyl group, a pentafluoroethyl group, or a cyano group; each of $A_1$ to $A_6$ and to $A'_1$ to $A'_6$ is independently a hydrogen atom, a methyl group, or an ethyl group; and each of k and h is independently 1 or 2).

3. A gate insulating film formed by using the forming agent for a gate insulating film of a thin film transistor as claimed in claim 2.

4. A thin film transistor comprising the gate insulating film as claimed in claim 3.

5. A gate insulating film formed by using the forming agent for a gate insulating film of a thin film transistor as claimed in claim 1.

6. A thin film transistor comprising the gate insulating film as claimed in claim 5.

* * * * *